United States Patent [19]

Manoury et al.

[11] Patent Number: 4,857,536
[45] Date of Patent: Aug. 15, 1989

[54] ANTIHISTAMINIC BENZIMIDAZOLE DERIVATIVES

[75] Inventors: Philippe Manoury, Verrieres le Buisson; Guy Rossey, Montigny le Bretonneux; Jean Binet, Breuillet; Gérard DeFosse, Paris; Najib Jabri, Courbevoie, all of France

[73] Assignee: Synthelabo, Paris, France

[21] Appl. No.: 222,758

[22] Filed: Jul. 22, 1988

[30] Foreign Application Priority Data

Jul. 23, 1987 [FR] France .................. 87 10409

[51] Int. Cl.$^4$ .................. A61K 31/445; C07D 401/04
[52] U.S. Cl. .................. 514/322; 544/331; 546/199
[58] Field of Search .................. 546/199; 514/322

[56] References Cited

U.S. PATENT DOCUMENTS 3,528,991 9/1970 Bell .................. 546/199 X

FOREIGN PATENT DOCUMENTS 0005318 11/1979 European Pat. Off. .
0145037 6/1985 European Pat. Off. .
0217700 4/1987 European Pat. Off. .

*Primary Examiner*—Richard A. Schwartz
*Attorney, Agent, or Firm*—Fleit, Jacobson, Cohn, Price, Holman & Stern

[57] ABSTRACT

A compound which is a benzimidazole derivative of formula (I)

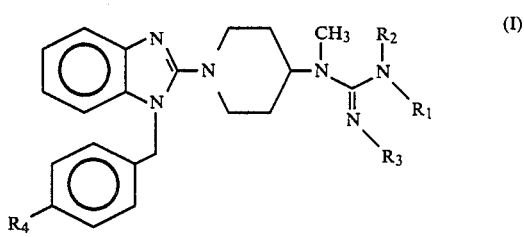

in which:
   $R_1$ is hydrogen or methyl,
   $R_2$ is hydrogen, methyl or acetyl,
   $R_3$ is hydrogen, methyl or acetyl, and
   $R_4$ is hydrogen or a halogen,
   or a pharmaceutically acceptable acid addition salt thereof.

The compounds have histamine antagonist activity and are also synthesis intermediates.

5 Claims, No Drawings

ANTIHISTAMINIC BENZIMIDAZOLE DERIVATIVES

The present invention relates to benzimidazole derivatives, to their preparation, to their application in therapy and to a process for preparing other benzimidazole derivatives from them.

The present invention provides a compound which is a benzimidazole derivative of formula (I)

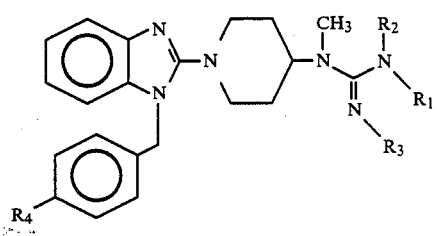

in which:
$R_1$ is hydrogen or methyl,
$R_2$ is hydrogen, methyl or acetyl,
$R_3$ is hydrogen, methyl or acetyl, and
$R_4$ is hydrogen or a halogen,
or a pharmaceutically acceptable acid addition salt thereof.

The tautomeric forms of the benzimidazole derivative of formula (I) also form part of the invention. Tautomeric forms exist, for example, when $R_1$ and/or $R_2$ and/or $R_3$ is a hydrogen atom. $R_2$ and $R_3$ may be considered equivalent when $R_1$ is hydrogen. $R_1$ and $R_2$ are equivalent due to rotation of the C—N bond.

$R_4$ is preferably fluorine and the addition salt is preferably a fumarate or acetate salt.

The compounds of formula (I) or pharmaceutically acceptable salts thereof may be prepared according to the reaction scheme shown in the appendix. The salts may be prepared in a conventional manner.

The present invention provides a process for preparing a compound of formula (I)a in which each of $R_1$, $R_2$ and $R_3$ is hydrogen, which comprises reacting a compound of formula (II) in which $R_4$ is as defined above with cyanamide.

The present invention also provides a process for preparing a compound of formula (I)b in which $R_1$ is hydrogen, $R_2$ is acetyl and $R_3$ is hydrogen or acetyl, which comprises reacting a compound of formula (I)a in which each of $R_1$, $R_2$ and $R_3$ is hydrogen and $R_4$ is as defined above with acetic anhydride.

The present invention further provides a process for preparing a compound of formula (I)a in which each of $R_1$, $R_2$ and $R_3$ is independently hydrogen or methyl, which comprises reacting a compound of formula (III) in which $R_3$ is hydrogen or methyl and $R_4$ is as defined above with ammonia, methylamine or dimethylamine.

The present invention additionally provides a process for preparing a compound of formula (I)b in which $R_1$ is methyl, $R_2$ is acetyl and $R_3$ is hydrogen, methyl or acetyl or $R_1$ is methyl, $R_2$ is hydrogen or methyl and $R_3$ is acetyl or $R_1$ is hydrogen, one of $R_2$ and $R_3$ is methyl and the other of $R_2$ and $R_3$ is acetyl, which comprises reacting a compound of formula (I) in which each of $R_1$, $R_2$ and $R_3$ is independently hydrogen or methyl with acetic anhydride.

The preparation of a compound of formula (II) in which $R_4$ is a halogen is described in the applicant's French patent application No. 85/13,453 (Publication No. 2,587,029). A compound wherein $R_4$ is hydrogen may be prepared in an analogous manner.

The examples which follow further illustrate the invention.

The structure of the compounds is confirmed by IR and NMR spectra.

EXAMPLE 1

N-[1-[1-[(4-fluorophenyl)methyl]-2(1H)-benzimidazolyl]-4-piperidinyl]-N-methylguanidine A mixture of 10.1 g (0.03 mole) of 1-[1-[(4-fluorophenyl)methyl]-2(1H)-benzimidazolyl]-N-methyl-4-piperidinamine with 1.4 g (0.032 mole) of cyanamide and 1.8 g (0.03 mole) of acetic acid is heated to 135° C. for 1.5 hours. The mixture is cooled and it is then taken up with methylene chloride under reflux, and the precipitate is filtered off and then dried. N-[1-[1-[(4-fluorophenyl)methyl]-2(1H)-benzimidazolyl]-4-piperidinyl]-N-methylguanidine acetate is thus obtained.

M.p. = 233° C. (propanol).

EXAMPLE 2

N-[1-[1-[(4-fluorophenyl)methyl]-2(1H),benzimidazolyl]-4-piperidinyl]-N-methyl-N'-acetylguanidine 0.85 ml of 5.3N sodium methylate is added to a suspension of 2 g (0.004 mole) of the product obtained above in 30 ml of methylene chloride and the solution is evaporated to dryness; the methanol-free residue is taken up with 30 ml of methylene chloride and the mixture is cooled to approximately 5° C. At this temperature, 0.43 ml of acetic anhydride dissolved in 5 ml of methylene chloride is added and the mixture is then stirred for 2 h while the temperature is kept at 5° C.

The mixture is neutralized with sodium methylate and the product is purified by chromatography on a silica column (eluent 9/1 methylene chloride/methanol).

N-[1-[1-[(4-fluorophenyl)methyl]-2(1H)-benzimidazolyl]-4-piperidinyl]-N-methyl-N'-acetylguanidine is thus obtained.

M.p. = 192° C.

EXAMPLE 3

N-[1-[1-[(4-fluorophenyl)methyl]-2(1H)-benzimidazolyl]-4-piperidinyl]-N,N'-dimethylguanidine

3.1.

N-[1-[1-[(4-fluorophenyl)methyl]-2(1H)-benzimidazolyl]-4-piperidinyl]-N,N'-dimethylthiourea 6.8 g (0.02 mole) of [1-[(4-fluorophenyl)methyl]-2(1H)-benzimidazolyl]-N-methyl-4-piperidinamine are heated under reflux, for 3 h, with 1.6 g (0.022 mole) of methyl isothiocyanate in 60 ml of ethanol.

The solution is evaporated to dryness and the residue is taken up with 50 ml of boiling toluene. On cooling, N-[1-[1-[(4-fluorophenyl)methyl]-2(1H)-benzimidazolyl]-4-piperidinyl]-N,N'-dimethylthiourea is obtained.

M.p. = 176° C.

3.2.

N[1-[1-[(4-fluorophenyl)methyl]-2(1H)-benzimidazolyl]-4-piperidinyl]-N,N'-dimethylguanidine The above product is dissolved in 15 ml of acetonitrile and 20 ml of methylene chloride. 0.6 ml of methyl iodide is added and the solution is left to stand overnight. The solution is evaporated to dryness and an oil is obtained, which is dissolved in 50 ml of a saturated ammoniacal ethanol solution. The solution is heated in an autoclave at 110° C. for 5 hours. It is evaporated to dryness, the residue is taken up with methylene chloride and is dried with MgSO$_4$, and is filtered and evaporated.

The fumarate of the compound is prepared in an ethanol/ether mixture.

M.p.=188° C. (propanol).

EXAMPLE 4

N-[1-[1-[(4-fluorophenyl)methyl]-2(1H)-benzimidazolyl]-4-piperidinyl]-N',N'-dimethyl-N''-acetylguanidine 0.48 ml of acetic anhydride dissolved in 5 ml of methylene chloride is added to a solution of 2 g (0.005 mole) of N-[1-[1-[(4-fluorophenyl)methyl]-2-(1H)-benzimidazolyl]-4-piperidinyl]-N,N'-dimethylguanidine in 20 ml of methylene chloride, cooled to 5° C. Stirring is continued for 2 h and the mixture is then poured into concentrated sodium hydroxide. The phases are separated, the organic phase is dried with MgSO$_4$, is filtered and is evaporated down. On addition of acetone, the product crystallizes. It is purified by chromatography on a silica column (eluent 9/1 methylene chloride/methanol) N-[1-[1-[(4-fluorophenyl)methyl]-2(1H)-benzimidazolyl]-4-piperidinyl]-N,N'-dimethyl-N''-acetylguanidine is obtained.

M.p.=203° C.

EXAMPLE 5

N-[1-[1-[(4-fluorophenyl]methyl]-2(1H)-benzimidazolyl)-4-piperidinyl]-N,N'-dimethyl-N',N''-diacetylguanidine The above crystallization filtrate is evaporated to dryness and the residue obtained is purified on a chromatography column.

N-[1-[1-[(4-fluorophenyl)methyl]-2(1H)-benzimidazolyl]-4-piperidinyl]-N,N'-dimethyl-N',N''-diacetylguanidine is obtained. M.p.=176° C.

Examples of compounds of the present invention are shown in the following table:

TABLE

| Compound | R$_1$ | R$_2$ | R$_3$ | R$_4$ | M.p. (°C.) | salt |
|---|---|---|---|---|---|---|
| 1 | H | CH$_3$ | H | F | 188 | fumarate |
| 2 | H | CH$_3$ | CH$_3$ | F | 235 | fumarate |
| 3 | CH$_3$ | CH$_3$—CO | CH$_3$—CO | F | 176 | — |
| 4 | H | CH$_3$ | CH$_3$—CO | F | 203 | — |
| 5 | CH$_3$ | CH$_3$—CO | H | F | 192 | — |
| 6 | H | H | H | F | 233 | acetate |

The compounds of the invention are both synthesis intermediates and also have a histamine antagonist activity.

The compounds of the invention allow the benzimidazole derivatives described in the applicant's French patent application No. 85/13,453 (Publication No. 2,587,029) to be prepared.

The present invention also provides a process for preparing a compound of formula (IV)

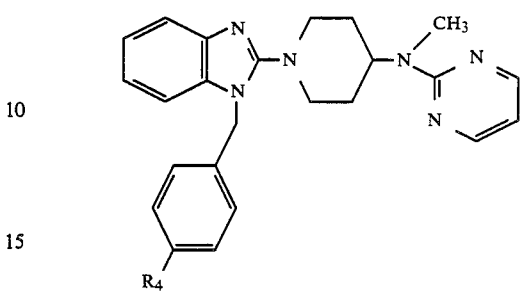

in which R$_4$ is as defined above and in which the pyrimidine ring may be unsubstituted or substituted, which comprises submitting a compound of formula (I) to conventional ring closure with the aid of an alkyl alkoxyacrylate, for example, a (C$_1$–C$_4$)alkyl (C$_1$–C$_4$)alkoxyacrylate.

The compounds of the invention have been subjected to various pharmacological tests to demonstrate their histamine antagonist activity.

1. Activity in vitro: isolated guinea pig ileum

The test has been performed according to Magnus's method as modified by Savini (Arch. Int. Pharmacodyn., 1957, 113, 157), on male three-coloured guinea pigs weighing approximately 300 g, fasted for 18 hours.

A fragment of ileum is removed, placed at 39° C. in a tyrode bath through which a stream of a mixture of oxygen and carbon dioxide (95% O$_2$, 5%, CO$_2$) is passed and connected to an isotonic sensor with a maximum tension of 2.5 g. The contractions are recorded using an Ugo Basile microdynamometer.

The contractions are induced by various spasmogenic agents, for which the concentration causing a submaximum response is determined (histamine: 1 to $8 \times 10^{-8}$ g/ml).

The compounds of the invention, dissolved in distilled water or a 0.1N solution of methanesulphonic acid, are placed in contact with the ileum for 1 min before the spasmogenic substance is introduced.

The AC$_{50}$ values (concentration reducing the histamine-induced contractions by 50%) of the compounds of the invention range from $10^{-7}$ to $10^{-8}$ molar.

2. Activity in vivo: inflammation induced by histamine

The intraplantar injection of histamine (2 mg) into one of the hind paws of the rat produces an oedema measured, 1 hour after the injection, with an Ugo Basile mercury plethysmometer.

The compounds according to the invention, suspended in Tween dissolved at a concentration of 1% in distilled water are administered p.o. (0.5 m/100 g) 1 hour before the injection of the inflammatory agent.

The AD$_{40}$ values (dose which reduces the volume of the oedema by 40%) of the compounds of the invention vary from 0.2 to 10 mg/kg. The compounds of the invention are low in toxicity. Their oral LD$_{50}$ is generally higher than 1000 mg/kg.

The compounds of the invention may thus be employed for the treatment of allergies such as respiratory allergies, cutaneous allergies, ocular allergies and various allergic symptoms.

The present invention provides a compound of formula(I) or a pharmaceutically acceptable acid addition salt thereof for use in a method of treatment of the human or animal body by therapy, especially for use in a method of treatment of an allergy. The present invention also provides the use of a compound of formula (I) or a pharmaceutically acceptable acid addition salt thereof in the manufacture of a medicament for the treatment of an allergy.

Certain compounds of the invention are highly selective for type H1 histamine receptors and are devoid of anticholinergic and antiserotoninergic activity in therapeutic dosages. They have a long period of activity and their oral bioavailability is very high.

The present invention provides a pharmaceutical composition comprising a compound of formula (I) or a pharmaceutically acceptable acid addition salt thereof and a pharmaceutically acceptable excipient. The composition may be administered orally or parenterally.

The daily dosage may range, for example, from 1 to 100 mg administered orally.

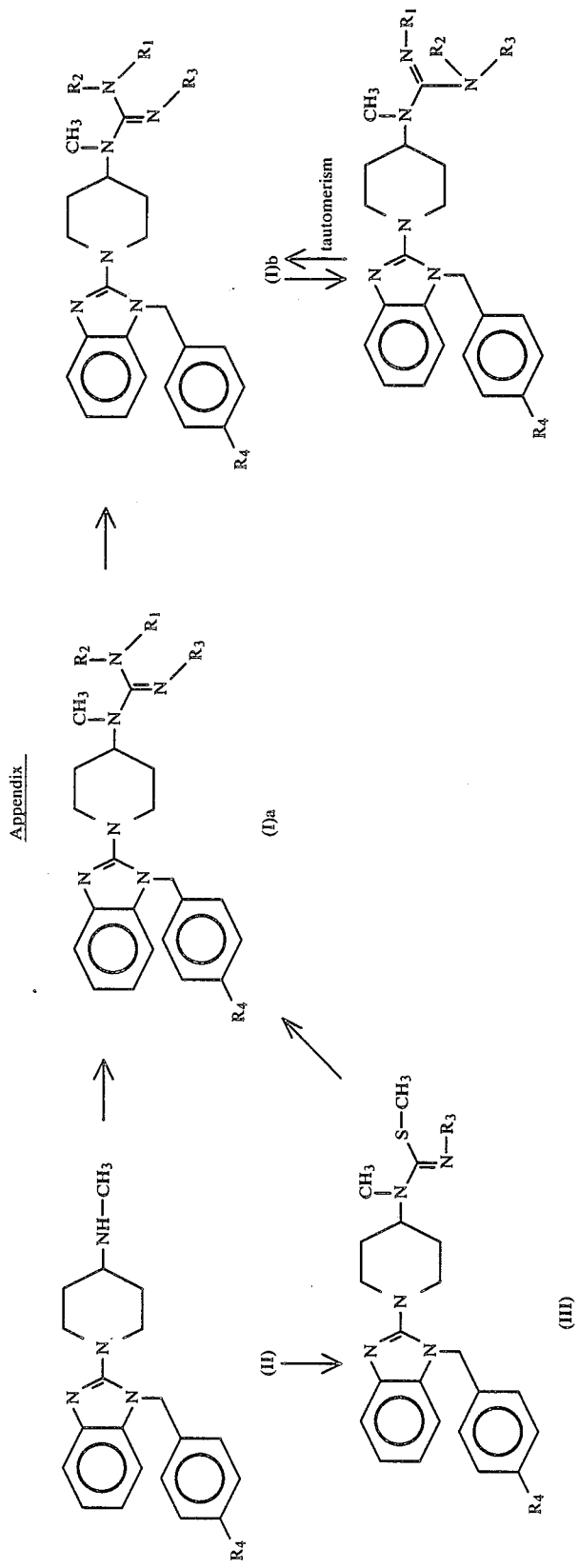

We claim:

1. A compound which is a benzimidazole derivative of formula (I)

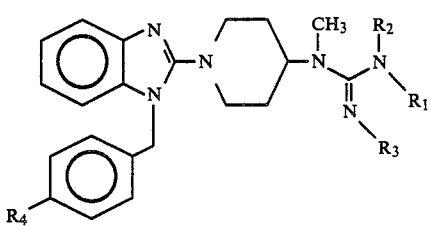

in which:
R₁ is hydrogen or methyl,
R₂ is hydrogen, methyl or acetyl,
R₃ is hydrogen, methyl or acetyl, and
R₄ is hydrogen or a halogen,
or a pharmaceutically acceptable acid addition salt thereof.

2. A compound according to claim 1 wherein R₄ is fluorine.

3. A compound according to claim 1 which is in the form of a fumarate or acetate salt.

4. A pharmaceutical composition comprising an effective histamine antagonist amount of a compound as defined in claim 1 and a pharmaceutically acceptable excipient.

5. A method of treatment of an allergy which comprises administering to a subject suffering or liable to suffer therefrom an effective amount of a compound as defined in claim 1.

* * * * *